United States Patent [19]

Minton et al.

[11] Patent Number: 4,997,852

[45] Date of Patent: Mar. 5, 1991

[54] METHOD AND COMPOSITION FOR ACHIEVING CANCER CHEMOPREVENTIVE AND CHEMOTHERAPEUTIC ACTIVITY

[75] Inventors: John P. Minton; Thomas E. Webb; Hussein M. Abou-Issa, all of Columbus, Ohio

[73] Assignee: Ohio State University Research Foundation, Columbus, Ohio

[21] Appl. No.: 436,049

[22] Filed: Nov. 13, 1989

Related U.S. Application Data

[63] Continuation-in-part of Ser. No. 89,568, Aug. 26, 1987, abandoned.

[51] Int. Cl.$^5$ ............... A61K 31/20; A61K 31/07
[52] U.S. Cl. ............................ 514/559; 514/578; 514/725
[58] Field of Search ............... 519/578, 559, 725

[56] References Cited

PUBLICATIONS

Walaszek et al., Carcinogenesis, 1986; 7:1463–1466.
Walaszek et al., Cancer Letters, 1986; 33:25–32.
Oredipe et al., Cancer Letters, 1987; 38:95–99.
Walaszek et al., Carcinogenesis, 1984; 5:767–772.
Walaszek et al., IRCS Medical Science, 1986; 14:677–678.
Levvy, Biochem. J., 1952; 52:464–472.
Moon et al., The Retinoids, vol. 2, New York:Academic Press, 1984; 327–371.
Hixson et al., Toxicol. Appl. Pharmacol., 1979; 47:359–365.
Abou-Issa et al., Biochem. Biophys. Res. Comm., 1986; 135:116–123.
Welsch et al., Diet, Nutrition, and Cancer, 1986; (B. S. Reddy and L. A. Cohen eds.) CRS Press, Boca Ratyon, Fla., pp. 1–21.
Schamberger, Diet, Nutrition, and Cancer, Diet, Nutrition, and Cancer, (B. S. Reddy and L. A. Cohen eds.) CRS Press, Boca Raton, Fla., pp. 43–62 (1986).
Moon et al., Cancer Res., 1976; 36:2626.
Matsui et al., Chem. Pharm. Bull., (Tokyo) 1972; 20:845–848.
Swanson et al., J. Pharmacol. Exptl. Therap., 1981; 219:632–637.
Abou-Issa et al., Biochem. and Biophys. Res. Comm., Sep. 29, 1989, 163:1364–1369.

Primary Examiner—Mary C. Lee
Assistant Examiner—Peter Davis
Attorney, Agent, or Firm—Emch, Schaffer, Schaub & Porcello Co.

[57] ABSTRACT

The present invention describes a protocol for achieving a very high degree of anticarcinogenic (chemopreventive and chemotherapeutic) activity through the combination of low suboptimal doses of a D-glucarolactone-based dietary anticarcinogen with low suboptimal doses of a retinoid-based anticarcinogen. Synergism is obtained by this combination and these two anticarcinogens can be employed at dosages far below toxic levels and at dosages that are practical as a food supplement.

11 Claims, 5 Drawing Sheets

EFFECT OF DIETS ON MEAN NUMBER OF TUMORS / RAT

✶ CONTROLS (CHOWDIET)
△ 1.5 % HPR
☐ 0.75 mmol/kg HPR + 1 % CGT
▨ 0.75 mmol/kg HPR + 2 % CGT EFFECT OF DIETS ON % RATS WITH TUMORS
* CONTROLS (CHOWDIET)
○ 1 % CGT
⬤ 2 % CGT
□ 0.75 mmol/kg HPR + 1 % CGT
▨ 0.75 mmol/kg HPR + 2 % CGT
△ 1.5 mmol/kg HPR
▲ 0.75 mmol/kg HPR EFFECT OF DIETS ON MEAN WEIGHTS OF RATS (gm)

✳ CONTROLS (CHOWDIET)
○ 1.0 % CGT
⊙ 2.0 % CGT
□ 0.75 mmol/kg HPR + 1 % CGT
▥ 0.75 mmol/kg HPR + 2 % CGT
△ 1.5 % HPR

METHOD AND COMPOSITION FOR ACHIEVING CANCER CHEMOPREVENTIVE AND CHEMOTHERAPEUTIC ACTIVITY

This is a continuation-in-part of copending application Ser. No. 07/089,568 filed on Aug. 26, 1987 now abandoned.

This invention relates generally to a dietary supplement for achieving a very high degree of cancer chemopreventive and chemotherapeutic activity and particularly relates to a combination of low suboptimal doses of a D-glucarolactone-based dietary anticarcinogen with low suboptimal doses of a retinoid-based anticarcinogen.

BACKGROUND OF THE INVENTION

The present invention is a continuation-in-part of parent patent application Ser. No. 089,568, filed Aug. 26, 1987.

One class of agents which has been shown to inhibit tumor induction and tumor growth in a number of systems are the glucarolactone compounds. Various glucarolactone-based compounds, including calcium glucarate (CGT), microencapsulated D-glucaro-1,4-lactone, potassium hydrogen glucarate and 2,4-di-0-acetyl-D-glucaro-1-lactone, are known to be effective as inhibitors of beta-glucuronidase in cells, blood, urine and in the intestine and liver. By inhibiting beta-glucuronidase less detoxified (that is glucuronidated) toxins are hydrolysed and therefore more toxins are excreted. As a result, such glucarolactone-based compounds are useful in the treatment and prevention of various types of cancer.

Dietary calcium glucarate, as a slow release form of glucarate, effectively inhibits from 50-70% the chemical induction of tumors in rodent skin, mammary glands, Walaszek et al., Carcinogenesis, 7:1463-1466 (1986), lung, Walaszek et al., Cancer Letters 33:25-32, (1986), and liver, Oredipe et al., Cancer Letters 38:95-99 (1988). (Also, Walaszek, Z. et al. Inhibition of 7,12-dimethylbenzanthracene-induced rat mammary tumorigenesis by 2,5-di-0-acetyl-D-glucaro-1,4:6,3-dilactone, an in-vivo beta-glucuronidase inhibitor. Carcinogenesis 5:767-772, (1984); and, Walaszek, Z., et al., Inhibition of N-methyl-N-nitrosourea-induced mammary tumorigenesis in the rat by a betaglucuronidase inhibitor. IRCS Medical Science 14: 677-678, (1986)).

Glucarate was the active moiety since under the conditions employed, since equimolar calcium as calcium gluconate had no effect. Maximal effect was observed when glucarate was fed throughout the initiation and promotion phases at a level of at least 4% (128 mmol/kg diet). The mechanism of action of glucarate is thought to be enhanced glucuronidation of initiating and promoting agents through equilibrium formation of the beta-glucuronidase inhibitor D-glucaro-1,4-lactone, Levvy, Biochem. J. 52:464-472 (1952).

A second class of agents which has been shown to act at high dosages to inhibit tumor induction and tumor growth in a number of systems are the retinoids, Moon et al., in The Retinoids (M. B. Sporn, A. B. Roberts and D. S. Goodman, Eds.) Vol. 2, pp 327-371, Academic Press, 1984. Retinoid-based compounds including retinylacetate, retinylmethyl ether, 13-cis-retinoic acid and N-(4-hydroxyphenyl) retinaminde (HPR), have similarly been investigated for their anticarcinogenic activity. The inhibition of mammary tumor induction in rats requires near toxic levels of vitamin A, or its metabolites, Hixson et al., Toxicol. Appl. Pharmacol. 47:359-365 (1979). (See also, Abou-Issa, H., et al., Anticarcinogenic effect of retinoids on 7,12-dimethylbenz(a)anthracene-induced mammary tumor formation and its relation to cyclic AMP-dependent kinase. Biochem. Biophys. Res. Commun. 135: 116-123, (1986); Welsch, C. W., et al., Retinoids and Mammary gland tumorigenesis in Diet, Nutrition and Cancer (B. S. Reddy and L. A. Cohen eds.) CRS Press Boca Raton, FL. pp 1-21, (1986); Schamberger, R. J., Chemoprevention of cancer in Diet, Nutrition and Cancer. (B. S. Reddy and L. A. Cohen eds.) CRC Press, pp. 43-62, (1986); and, Moon, R. C., Inhibition of 7,12-dimethylbenzanthracene-induced mammary carcinogenesis by retinyl acetate. Cancer Res. 36:2626, (1976)).

These studies confirm the activity of relatively high doses of retinoids against the chemical induction of mammary carcinogenesis in the rat. Similarly, high dosages were tested against the chemical carcinogen-mediated induction of tumors in the mammary gland, lung, skin, intestine and liver. Further, retinoids have been shown to protect skin, nasopharnyx, lower respiratory tract, urinary bladder and colon against carcinogens. In addition, these retinoic acid analogs (Vitamin A active compounds) have been tested in combination with the micronutrient selenium.

One problem associated with the use of retinoid-based compounds is that relatively high doses of the retinoids must be administered in order to achieve the desired anticarcinogen effect. Such high doses of retinoids often results in cummulative toxicity, with the excess retinoids being deposited in the liver.

However, there has been no suggestion in the art that a combination of glucarolactone-based compounds and retinoid-based compounds would be especially useful as anticarcinogens; that is, that the combination of these compounds would represent an alternative for use in the prevention of cancer or for use in the therapeutic treatment of cancer.

It has now been found that the use of a combination of glucarolactone-based compounds and retinoid-based compounds or their pharmaceutically-acceptable salts and esters, compounds which are known to be safely administered to humans and animals, significantly reduce the incidence of tumors and further prevent the formation of cancer.

Since glucarate, as end product of glucuronic acid metabolism and a component of fruits and vegetables is normally present in the body at low levels, Matsui et al., Chem. Pharm. Bull (Tokyo) 20:845-848 (1972) and excreted in the urine, we investigated to determine whether it had chemopreventive and/or therapeutic activity in combination with natural metabolites of vitamin A. A synergistic effect between CGT and the synthetic analog N-(4-hydroxyphenyl)retinamide (HPR) which exhibits activity of vitamin A and its metabolites have been observed for both chemoprevention of DMBA-induced rat mammary tumors, Swanson et al., J. Pharmacol. Exptl. Therap. 219:632-637 (1981). The present invention, in part, shows the synergistic effect between CGT and HPR for growth arrest and shrinkage of pre-established rat mammary tumors. The dietary levels at which the synergistic effect is observed were 32-64 mmol/kg diet of CGT and 0.75 mmol/kg diet of HPR. This compares with 128 mmol/kg CGT and 2.00 mmol/kg HRP when used individually. The present invention also shows that the combinations of low nontoxic doses of two natural compounds act synergistically and are effective anti-cancer and chemopreventative agents, both in vivo and in vitro.

It is therefore an object of the present invention to provide a safe and effective method for inhibiting the formation of tumors, inhibiting (or shrinking) tumor growth, and reducing the incidence of cancer in certain high risk populations.

Other objects and advantages of the invention will be apparent from the following detailed description of the invention.

SUMMARY OF THE INVENTION

The present invention describes a protocol for achieving a very high degree of anticarcinogenic (chemopreventive and chemotherapeutic) activity through the combination of low suboptimal doses of a D-glucarolactone-based dietary anticarcinogen with low suboptimal doses of a retinoid-based anticarcinogen. Synergism is obtained by this combination and the combination of these two anticarcinogens can be employed at dosages far below toxic levels and at dosages that are practical as a food supplement.

DESCRIPTION OF INVENTION

Figure 1:
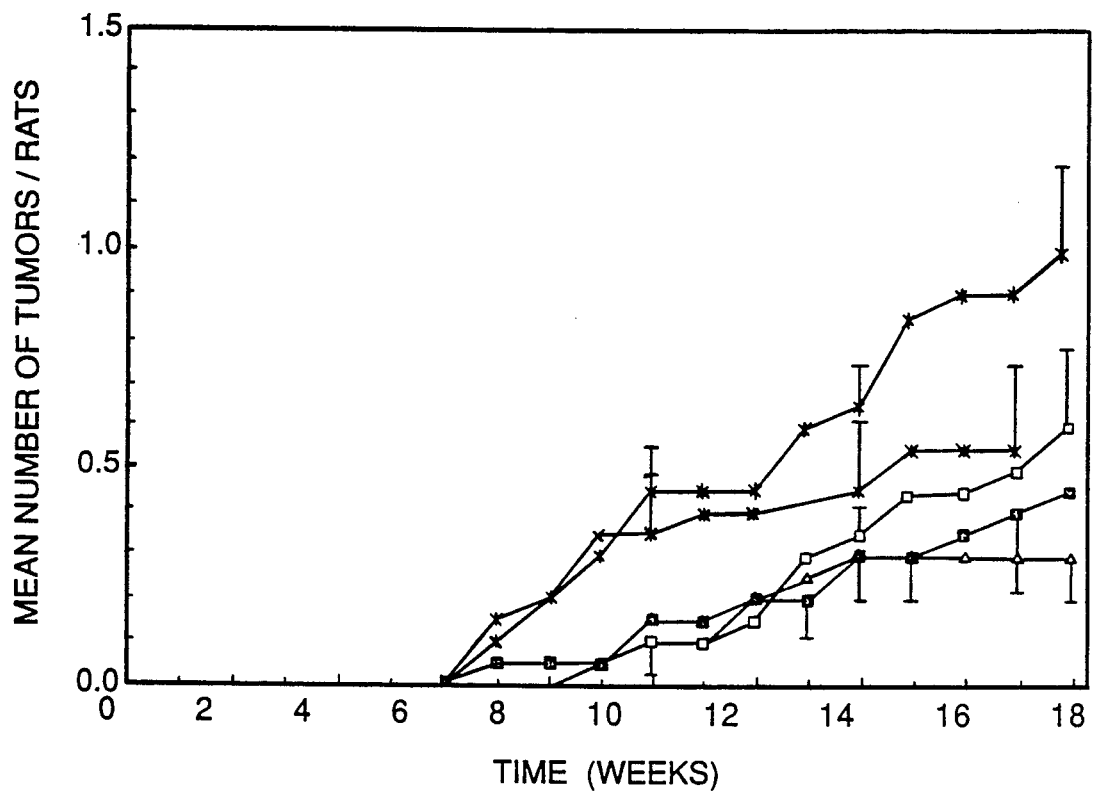
FIG. 1 is a graph showing the effect of diets on the mean number of tumors per rat: * control (chow diet); △ 1.5% HPR; ☐ 0.75 mmol/kg HPR and 1% CGT; and, ■ 0.75 mmol/kg HPR and 2% CGT.

The present invention relates to a method for achieving a very high degree of anticarcinogenic activity, both chemopreventive and chemotherapeutic, comprising the administration of a safe and effective amount of a compound comprising a combination of a D-glucarolactone-based dietary anticarcinogen with a retinoid-based anticarcinogen and pharmaceutically-acceptable salts and esters thereof to a subject either in a high risk group for cancer or to a subject who has cancer.

The treatment regimens encompassed by the present invention employ a safe and effective amount of a pharmaceutically-acceptable composition comprising a combination of a glucaro-lactone-based and a retinoid-based compound. These compounds are administered to prevent the occurrence of cancer and to inhibit the growth of cancer tumor cells in humans and animals. Various glucarolactone-based compounds utilized herein are conveniently abbreviated "glucarolactone", calcium glucarate as "CGT", potassium hydrogen glucarate as "GT" or D-glucaro-1,4-lactone as "GL"; various retinoid-based compounds utilized herein are conveniently abbreviated "retinoids", N-(4-hydroxyphenyl)retinamide as "HPR" or 13-cis-retinoic acid as "13-cis-RA". The phase "safe and effective amount of glucarolactone/retinoid compound" herein, means sufficient glucarolactone/retinoid compound to desirably affect and inhibit the induction or growth of tumor cells and to desirably affect or shrink tumor cells already present, at a reasonable benefit/risk ratio attendant with any medical treatment. Within the scope of sound medical judgment, the required dosage of the glucarolactone/retinoid compound will vary with the severity of the condition being treated, the duration of the treatment, the nature of adjunct treatment, the age and physical condition of the patient, the specific glucarolactone and retinoid compounds employed, and like considerations discussed more fully hereafter.

"Pharmaceutically acceptable", as used herein, means that the glucarolactone/retinoid compound and other ingredients used in the compositions employed herein are suitable for use in contact with the tissues of humans and lower animals without undue toxicity, irritation, allergic response, and the like, commensurate with a reasonable benefit/risk ratio.

The term "administration" of the glucarolactone/retinoid compounds and compositions, as used herein includes intragastric and oral administration thereof.

The term "comprising", as used herein, means that various other compatible drugs and medicaments, as well as inert ingredients, can be conjointly employed in the therapeutic methods of this invention, as long as the critical glucarolactone/retinoid compounds are used in the manner disclosed. The term "comprising" thus encompasses and includes the more restrictive terms "consisting of" and "consisting essentially of".

By "compatible", herein, it is meant that the components of the composition used in the practice of this invention are capable of being comingled without interacting in a manner which would substantially decrease the efficacy of the glucarolactone/retinoid compositions under ordinary use situations.

The novel compositions of the invention are useful for the treatment of various cancers, such as for example, lung, colon and mammary cancers. The novel compositions may be used alone or in combination with other therapeutic agents active for these purposes. As used herein, the term "inhibition" comprehends arresting or retarding the growth of the malignacy or other manifestation of a disease, as compared with the course of the disease in the absence of treatement.

The novel compositions of the present invention are also useful to prevent the occurence of cancer in high risk populations. The compositions may be used alone or in combination with other chemopreventative agents active for these purposes. As used herein, the term "prevention" comprehends reducing the incidence of tumors in a patient or a population exposed to cancer causing agents such as cigarette smoking, or environmental toxins, as compared with the course of potential development of this disease in the absence of treatment. It also comprehends reducing endogenously produced cancer-causing agents including steroid hormones.

The mechanism of action of retinoid-based compounds such as 13-cisretinoic acid (13-cis-RA), retinylacetate retinylmethyl ether and N-(4-hydroxyphenyl) retinamide (HPR) are believed to act by inducing differentiation. One of the main biochemical effects of the retinoid-based compounds is to elevate the level of cellular cAMP (cyclic AMP) and of histone kinases.

Similarly, the glucarolactone-based compounds such as calcium glucarate, potassium hydrogen glucarate, micro-encapsulated D-glucaro-1,4-lactone, 2,4-di-O-acety-D-glucaro-1,4-lactone, when fed slowly release D-glucaro-1,4-lactone (GL), a potent inhibitor of beta-glucuronidase in the cells, blood and urine and in the intestine. Since beta-glucuronidase is inhibited, less detoxified (i.e., glucuronidated) toxins are hydrolyzed and therefore more toxins are excreted. Thus, the inhibition of beta-glucuronidase promotes clearance/excretion of detoxified (glucuronidated) compounds from the body. Not only carcinogens but other toxins, steroid hormones and other substances which undergo glucuronidation may be affected.

The above-mentioned compounds are used as dietary sources of GL since they are more effective by virtue of the fact they are sustained (slow)-release forms, GL itself being too rapidly absorbed and cleared from the body. Thus, the glucarolactone-class of inhibitors may be used to reduce the inappropriate level of any compound in the body which is subject to glucuronidation before excretion. Besides the glucarates, micro-encapsulated GL and the di-0-acetyl derivative of GL, dietary substances which may yield GL and which might be as useful as CGT include D-glucuronic acid, D-galacturic acid, L-iduric acid or derivatives or analogs thereof.

Although CGT in one embodiment of the invention is combined with retinoids it is also possible that CGT may be effectively combined with other micronutrients or even lower doses of CGT and retinoid may be combined with additional anticarcinogens. For example, calcium appears to be an anticarcinogen for colon cancer by ameliorating the toxic effects of bile acids so that the calcium glucarate/retinoid combination may be considered to be a combination of three anticarcinogens, though the protective effect of these low dosages of calcium are minimal.

A particularly interesting combination is CGT/retinoid/ascorbic acid, since Vitamin C is protective against colon cancer. Because of activity against carcinogens attacking most major organs, whereas other anticarcinogens are more organ-specific, the glucarolactone-based/retinoid-based anticarcinogens can serve as a common component in combinations with other known anticarcinogens.

A combination of low non-toxic doses of dietary retinoid (HPR) and dietary calcium glucarate inhibited the incidence of dimethyl benz (a) anthracene-induced rat mammary tumors to a greater extent than the same doses of either agent alone. This combination was also able to reduce the number of palpable tumors by one-half (50%) as compared to rats that received the control diet, or identical doses of either agent alone. These results, which are relevant to breast cancer, also apply to chemoprevention of cancer at other sites, including higher doses of CGT which have been shown to be effective against lung, colon and mammary carcinogenesis while retinoids are known to be effective against mammary and colon carcinogenesis.

A combination of suboptimal doses of retinoid and glucarolactone-based dosage of the anti-cancer agents, both toxicity and impractical dosage requirements are circumvented.

EXAMPLE I

The following example demonstrates the heretofore unsuspected ability of the composition of the present invention to desirably inhibit the formation of tumors. The effect of CGT, HPR and CGT/HPR on 7,12-dimethylbenz(a)anthracene(DMBA)-induced mammary tumor formation in female Sprague Dawley rats was determined using the following protocol: Female rats maintained on one of 8 diets received 75 mg/kg of 7,12-dimethylbenz(a)anthracene in mineral oil by mouth. They were maintained on the diets for approximately 4 mos., and were examined (palpated) for mammary tumors weekly. The diets were (i) rat chow; (ii) chow and 1% CGT; (iii) chow and 2% CGT; (iv) chow and 4% CGT; (v) chow and 0.75 mmol/kg HPR; (vi) chow and 1.5 mmol/kg HPR; (vii) chow and 1% CGT and 0.75 mmol/kg HPR; and (viii) chow and 2% CGT and 0.75 mmol/kg HPR. Note: mmol/kg means mmol/kg diet; 1% CGT means 1gm/100gm of chow. In these experiments the CGT powder was mixed into the powdered chow diet. The retinoid (HPR) was first dissolved in 25 ml of a vehicle consisting of ethanol-tricaprylin-6% α-tocopherol, then thoroughly mixed with powdered rat chow. The results obtained, expressed in tumor incidence, total number of tumors, and tumors per rat, are summarized in the following Table I:

TABLE I

Effect of CGT, HPR and CGT & HPR on 7,12-Dimethylbenz(a)anthracene-induced Mammary Tumor formation in Female Sprague Dawley Rats

| Dietary Anti-carcinogen | No. of Rats | Rats with Tumors | Tumor Incidence | Total No. Tumors | Tumors Per Rat |
| --- | --- | --- | --- | --- | --- |
| None (control) | 20 | 14 | 70 | 22 | 1.1 |
| 1% CGT | 20 | 11 | 55 | 20 | 1.0 |
| 2% CGT | 20 | 11 | 55 | 20 | 1.0 |
| 4% CGT | 20 | 7 | 35 | 10 | 0.5 |
| 0.75 mmol/kg HPR | 20 | 12 | 60 | 20 | 1.0 |
| 1.5 mmol/kg HPR | 20 | 6 | 30 | 7 | 0.35 |
| 0.75 mmol/kg HPR & 1% CGT | 20 | 9 | 45 | 12 | 0.6 |
| 0.75 mmol/kg HPR & 2% CGT | 20 | 7 | 35 | 9 | 0.45 |

% CGT = gm % of calcium glucarate added to chow diet. mmol/kg HPR = moles of 4-hydroxy phenyl-retinamine added to chow diet per kg diet.
Protocol: 50 d old female S.D. rats received a single dose 75 mg/kg of DMBA. Feeding of CGT, HPR or both was initiated 2 weeks before treatment with DMBA, then continued throughout the experiment.

When tested alone the higher doses of CGT (4%) and HPR (1.5 mmol) markedly inhibited tumorigenesis i.e., tumor incidence by 50-60% and tumors/rat by 50-65%. At lower doses the effect was minimal i.e., 1.0% CGT inhibited tumor incidence only 20% and tumors/rat by 9% while 0.75 mmol/kg HPR inhibited tumor incidence only 15% and tumors/rat by 9%. In contrast, when tested in combination, 1% CGT and 0.75 mmol/kg HPR inhibited tumor incidence by 36% and tumors/rat by 45%. Similarly 2% CGT and 0.75 mmol/kg HPR inhibited tumor incidence by 50% and tumors/rat by 60%.

Figure 2:
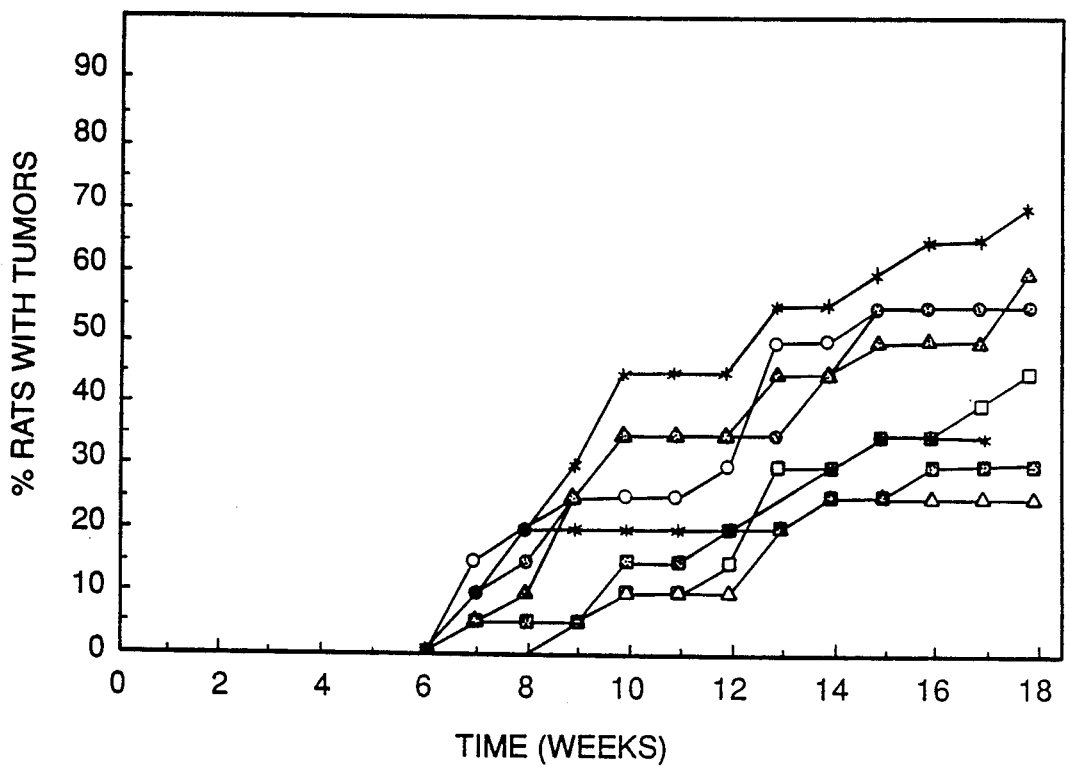
FIG. 2 is a graph showing the effect of diets on the percentage of rats with tumors: * control (chow diet); ○ 1% CGT; ● 2% CGT; ☐ 0.75 mmol/kg HPR and 1% CGT; ■ 0.75 mmol/kg HPR and 2% CGT; △ 1.5 mmol/kg HPR; and ▲ 0.75 mmol/kg HPR.

The effect of the diets on the mean number of tumors per rat is shown in FIG. 1, while FIG. 2 shows the effect of the diets on the percent of rats with tumors.

Glucarolactone-based inhibitors acts to inhibit the growth of hormone-dependent tumors by lowering hormone levels. It has previously been shown in Walaszek, Z., et al., Carcinogenesis 7:1463-1466 (1986), that dietary calcium glucarate (CGT) inhibits the promotion phase of 7,12-dimethylbenz(a)anthracene-induced mammary tumorigenesis. The female rats were put on the CGT diet two weeks after treatment with carcinogen. By 28 weeks tumor induction in the rats on the 4% CGT diet was only 30% of that in the controls, indicating CGT markedly inhibits the promotion phase in this model. Rats on the CGT-supplemented diet ate quantities of food and had weight gain identical to those on the normal chow diet. The anti-promotional effect of CGT was shown to be probably due to the reduction in the steady-state level of sex hormones. Further, and of relevance to this invention, some tumors on the chow diet supplemented with CGT underwent regression. The overall tumor incidence represents those which escape the anti-promotional effects of CGT and the equilibrium between growth and regression.

Figure 3:
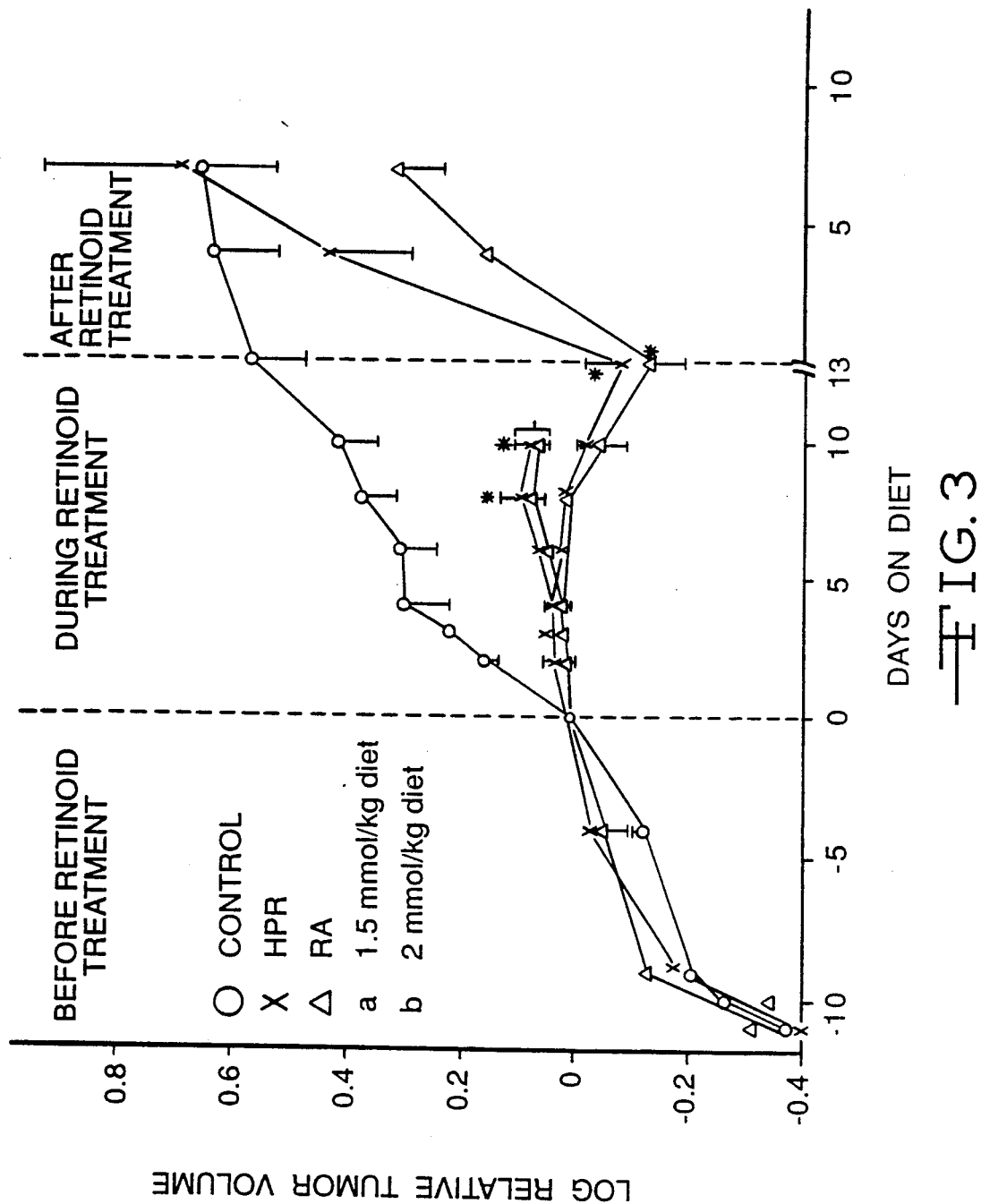
FIG. 3 is a graph showing the effects of retinoids on inhibiting growth of established cancer, before retinoid treatment, during retinoid treatment and after retinoid withdrawal: ○ control; X HPR; △ RA; (a) 1.5 mmol/kg diet, (b) 2 mmol/kg diet.

Similarly, retinoids, as shown in FIG. 3, inhibit growth of established cancer. The administration of 1.0 mmol/kg diet of HPR daily to female Sprague Dawley rats with already established DMBA-induced mammary tumors resulted in 80-90% inhibition of tumor growth within 10 days. Similarly, when given to $CD_8F_1$ mice with established mammary tumors this retinoid resulted in 50% inhibition of tumor growth. When higher doses (2 mmol/kg diet) of HPR were used, growth arrest was followed within 5 to 10 days by 30% regression of the DMBA-induced mammary tumors. Also, HPR ($0.1\mu M$) inhibited the in vivo growth of the human breast cancer cell line (MCF-7) to 50% of the control within 7 days. These results suggest that retinoids have anti-tumor effects besides their cancer chemopreventive effects.

Figure 4:
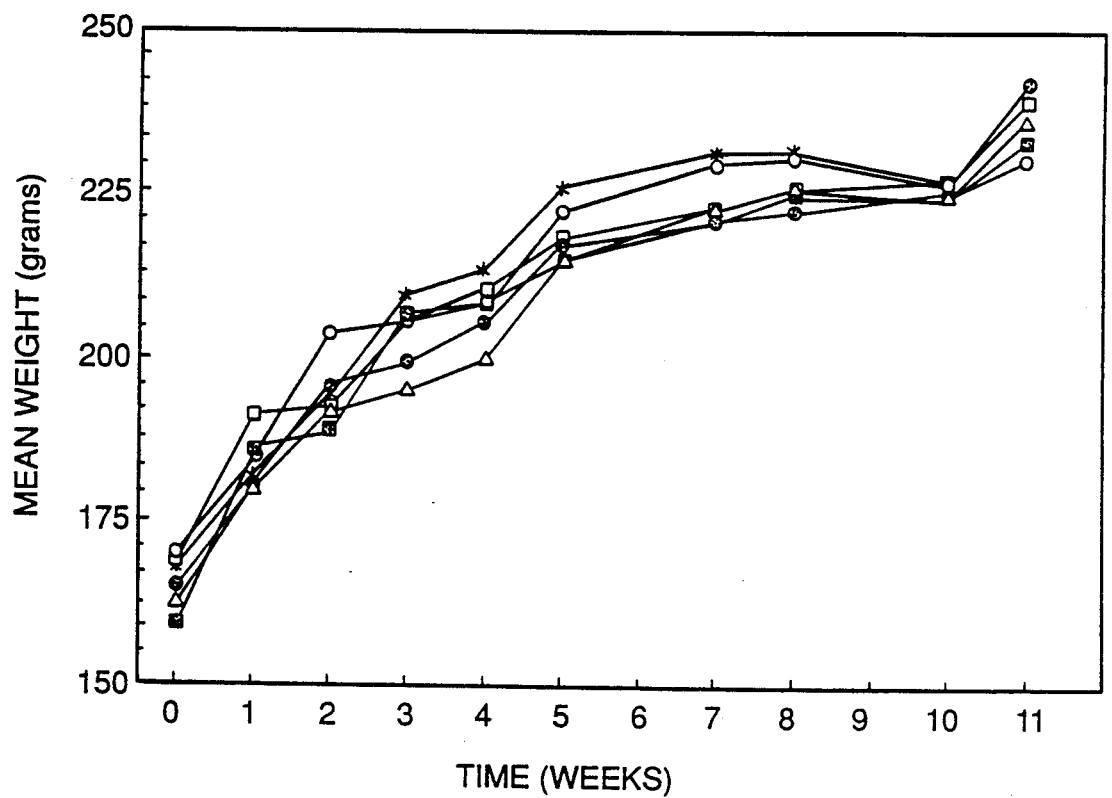
FIG. 4 is a graph showing the effect of diets of the mean weight of rats: *control (chow diet); ○ 1.0% CGT; ● 2.0% CGT; ☐ 0.75 mmol/kg HPR and 1% CGT; ■ 0.75 mmol/kg HPR and 2% CGT; and △ 1.5% HPR.

As shown in FIG. 4 prolonged feeding of diets containing CGT and HPR did not affect weight gain of rats. This is important since toxicity as evidenced by marked weight loss may also influence carcinogenesis and tumorigenesis.

The effect glucarolactone (GL) alone or in combination with HPR on the growth of MCF-7 cells is shown in Table II below. The cells were plated at the density of 3775 cc per well in six well plates and treated after one day with GL-, HPR-or GL and HPR- containing media for 5 days. The values shown are the mean +/− 1SE for three experiments counted in triplicates. The numbers in parenthesis indicate the number of free floating (mostly non viable) cells in the media. As can be seen, the GL/HPR-containing media had only one-third the viable cells as the control medium. The GL ($10^{-4}M$)/HPR($5\times10^{-8}M$)-containing medium had nearly one-third the viable cells as the GL ($10^{-4}M$) medium alone and had nearly one-half the viable cells as the HPR($5\times10^{-8}M$) medium alone. These experiments indicate that the combination of GL and HPR is capable of inhibiting tumor cell growth and that such combination is more effective than either the GL- or HPR-containing media alone in inhibiting tumor cell growth.

TABLE II

| Treatment | No. of viable cells | % of control |
|---|---|---|
| 0.1% Ethanal | 60400 ± 2147 (6440) | 100 ± 4 (11) |
| GL ($10^{-4}$ M) | 49480 ± 3160 (3440) | 82 ± 5 (6) |
| GL ($10^{-3}$ M) | 32560 ± 1800 (4560) | 54 ± 3 (7) |
| HPR ($5 \times 10^{-8}$ M) | 33680 ± 2627 (4160) | 56 ± 4 (7) |
| GL ($10^{-4}$ M) + HPR ($5 \times 10^{-8}$ M) | 18160 ± 1568 (5280) | 30 ± (9) |
| GL ($10^{-3}$ M) + HPR ($5 \times 10^{-8}$ M) | 22680 ± 1863 (2960) | 37 ± 3 (5) |

EXAMPLE II

The following example demonstrates the ability of the composition of the present invention to desirably inhibit the formation of tumors and to desirably inhibit tumor growth. Female rats of the Sprague Dawley strain of 50 days of age were treated each with DMBA (75 mg/kg body weight in 1.0 ml of sesame oil by gavage) and randomized into 4 groups of 20 rats each which were maintained on the following diets: Group I: chow and vehicle; Group II: chow and 2% CGT (64 mmol/kg diet) and vehicle; Group III: chow and 1.0 mmol/kg 13-cis-RA and vehicle; Group IV: chow and 1.0 mmol/kg 13-cis-RA and 2% CGT and vehicle. The 13-cis-RA was dissolved in a vehicle consisting of ethanol:tricaprylin:1:4 (v/v) and 4% w/v α-tocopherol. The mixture was added to the meal at the rate of 25 ml/2 kg then stored in the dark at −20° C. The calcium glucarate was obtained from Gallard-Schlessinger, N.Y. and the 13-cis-RA from Hoffman-LaRoche, Nutley, N.J. The additives were incorporated into the diet with a mechanical mixer. The same amount of vehicle was also added to the control diet and to the diets containing glucarate. Beginning 5 weeks post DMBA treatment, the rats were examined (palpated) twice every week for mammary tumors. They were also weighed once weekly throughout the 20 week period of the experiment.

Figure 5:
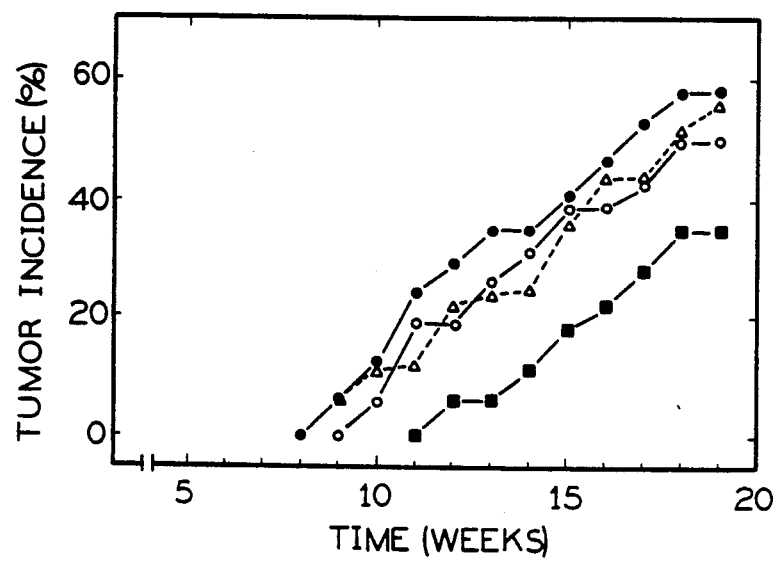
FIG. 5 is a graph showing the effects of diets on tumor incidence on the following (group; dosage in mmol/kg diet; symbol): I, control, basal chow diet ●; II, show +64 mmol/kg CGT △; III, chow +1.0 mmol/kg (300 mg/kg diet) 13-cis-RA (○); IV, chow +64 mmol/kg CGT +1.0 mmol/kg 13-cis-RA ▲.

The data in FIG. 5 present the cumulative tumor incidence (% rats with tumors) over the 20 week experiment. FIG. 5 shows the synergism between dietary calcium glucarate (dCGT) and 13-cis-retinoic acid (13-cis-RA) in chemoprevention of DMBA-induced rat mammary carcinogenesis.

Feeding a basal chow diet supplemented with 2% CGT, i.e. 64 mmol/kg diet (II) a suboptimal concentration of the agent, did not show any effect on tumor incidence compared to the control group (I). A suboptimal concentration (1.0 mmol/kg diet) of 13-cis-Ra (III) caused a slight, but insignificant, enhancement of tumor incidence over the controls (I). In contrast, in combination (IV) they caused a significant (4 week) delay and a 42% inhibition of tumor incidence.

Weight gain/food intake may affect tumor growth as reported in Table III below shows are the weights of the rats at selected time periods after the start of the experiment. There was no significant difference in the weight gain of the groups on the various diets over the course of the experiment.

TABLE III

| Diet (group) | | Weights (gm) of Rats on Diets Time on diets (weeks) | | |
|---|---|---|---|---|
| | | 0 | 5 | 17 |
| (I) | Chow + vehicle | 177.2 +/−10.9 | 218.3 +/−16.9 | 247.0 +/−32.2 |
| (II) | Chow + CGT | 182.2 +/−8.8 | 224.8 +/−11.6 | 250.3 +/−14.2 |
| (III) | Chow + RA | 176.8 +/−10.3 | 223.1 +/−17.3 | 255.7 +/−19.5 |
| (IV) | Chow + RA + CGT | 174.4 +/−14.5 | 216.1 +/−18.2 | 252.8 +/−26.3 |

EXAMPLE III

The following example illustrates the ability of the composition of the present invention to desirably inhibit cell growth of cancer cells. The MCF-7 cell line was derived from a hormone-dependent metastatic breast cancer. It has retained several characteristics of differentiated mammary epithelium, Soule et al., J. Natl. Cancer Inst. 51:1409–1413 (1973), and the cells contain estrogen receptors. The MCF-7 cell line used was obtained from the OSU Cell Culture Service laboratory, but originated from the Michigan Cancer Foundation, Detroit, Mich. The MCF-7 cells were seeded at $1 \times 10^3$ cells/cm$^2$ in 35 mm wells containing MEM (Earle base medium) supplemented with MEM non-essential amino acids (1.0 mM), L-glutamic acid (2.0 mM), penicillin and streptomycin (100 ug/ml) and fetal calf serum (10%) as described in Ueda et al., Cancer 46:2203–2206, (1980). The cells are maintained at 37° C. in a humidified atmosphere of 5% $CO_2$/20% $O_2$ with the growth medium replaced twice a week. The retinoids were dissolved in ethanol and added to the culture medium starting 24 hrs. after seeding. The retinoid concentration varied over the range $10^{-6}$ to $10^{-8}$M and the concentration of ethanol did not exceed 0.1%. Glucarate concentrations varied from $10^{-5}$ to $10^{-8}$M. Cell counts were done with a Coulter counter and viability of the cells was determined by the trypan blue exclusion method and also by their ability to resume growth after removal of inhibitory agents. Cytotoxicity was evaluated by exposing the MCF-7 cells to equimolar concentrations of the agents and examining viability after 6 days of treatment. All experiments were done in triplicate.

In this experiment series glucarate as the soluble potassium salt and 13-cis-RA were evaluated, alone and in combination, for their ability to inhibit the growth of MCF-7 breast cancer cells in culture.

Figure 6:
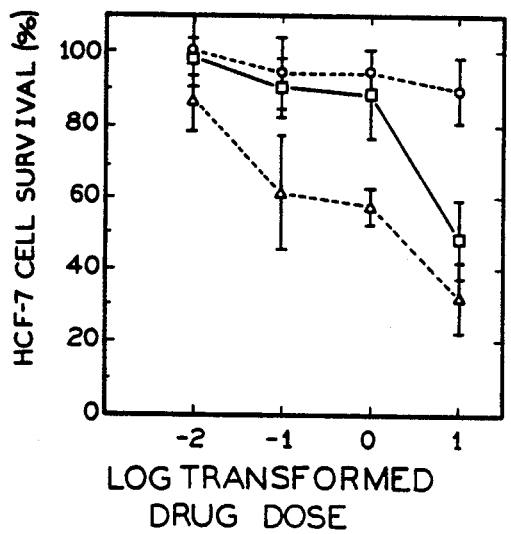
FIG. 6 is a graph showing the effect on MCF-7 cell survival of varying concentrations of glucarate (○), 13-cis-RA (☐) and their combination (△).

FIG. 6 shows the effect on MCF-7 cell survival of varying the concentration of glucarate (O), 13-cis-RA (□) or their combination (Δ) at the concentrations indicated. The log transformed dose refers to the level in μM added to the medium as was varied from $10^2$ (0.01) μM to $10^{-1}$ μM. The retinoid vehicle, ethanol, was added to all cultures and all values have been corrected for its slight inhibitory effect (7%).

As shown in FIG. 6, when added to the growth medium alone, 0.01, 0.1, 1.0 and 10 μM glucarate (GT) inhibited cell growth only by 0, 6, 6 and 11% respectively in the presence of 0.1% ethanol. Over the same range of concentrations, 13-cis-RA alone inhibited growth of the MCF-7 cells 2, 9.2, 12 and 52.2%, respectively. Thus, at concentrations above 1.0 μM, the retinoid alone exhibits significant inhibitory activity in this system. In combination, GT and 13-cis-RA showed significant synergistic activity in the inhibition of cell growth in a range between 0.01 and 10 μM. For example, when both compounds were added at 0.1 or 1.0 μM, MCF-7 cell growth was inhibited by 35% and 43%, respectively. This is significantly higher than would have occurred from the additive effects (15.2 and 18%, respectively) of each agent.

Figure 7:
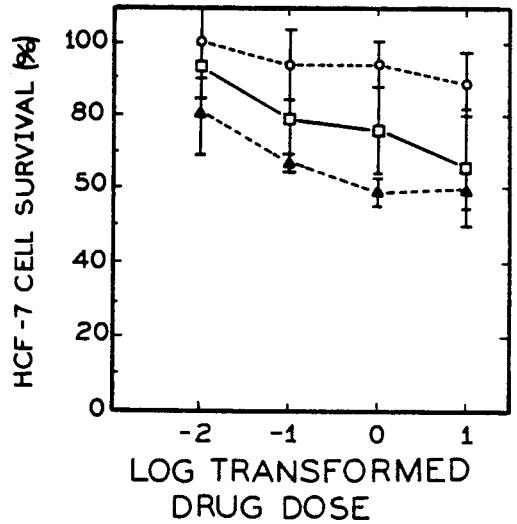
FIG. 7 is a graph showing the effect on MCF-7 cell survival of increasing the concentration of glucarate concentration in the medium while 13-cis-RA was held at 0.0 μM (○), 0.1 μM (◇) and 1.0 μM (△).

FIG. 7 shows the effect of increasing the concentration for glucarate in the medium when the concentration of added 13-cis-RA is held at 0.0 μM (O), 0.1 μM (◇) and 1.0 μM (Δ). Other conditions were the same as for described for FIG. 6. The present inhibition of growth as a function of the concentration of glucarate at all 3 concentrations of 13-cis-RA increased only moderately (7–25%) over the 1000-fold range in concentration evaluated. Furthermore, most of this increase occurred around 0.01 mM GT and the curves are roughly parallel. Taken together, these results show that glucarate has an adjuvant or modulator role and the retinoid is the effector.

The results shown in Examples II and III show that the synergism observed between CGT and the synthetic retinoid analog, HPR, in in vivo experiments can be duplicated with CGT and the natural vitamin A metabolite, 13-cis-RA. The Examples II and III confirm that this synergistic interaction occurs in vitro in tissue culture. Collectively, the data show that this synergistic combination acts directly on the cell rather than through a general systemic effect. This synergistic combination is effective both in preventing transformation of cells (or in delaying the progression of initiated cells), and in inhibiting the growth of tumor cells. The site of action of glucarate has not yet been indentified and its only known activity to date is its inhibition of beta-glucuronidase through equilibrium formation of D-glucaro-1, 4-lactone, a potent beta-glucuronidase inhibitor. There may very well be other sites of action. Retinoids are known to induce differentiation or apoptosis i.e., programmed cell death, Cho et al., Reviews on Endocrine-Related Cancer, 28:13–18 (1988). Retinoids inhibit the neoplastic transformation of mammary epithelium in whole organ culture, Dickens et al., Proc. Natl. Acad. Sci., 76:5891–5895 (1979), and inhibit the prolactin-induced increase in DNA synthesis in these glands. Again the antiproliferative effect of retinoids on the mammary epithelium is shown by a significant inhibition of ductal branching and end-bud proliferation, Mehta et al., Carcinogenesis, 4:23–26 (1983). The in vitro example shown herein also suggests that retinoids inhibit the proliferation and reverse the altered differentiation of some transformed cells.

The nature of the interaction between 13-cis-RA and glucarate is not clear. The glucarate is believed, through equilibrium conversion to D-glucaro-1, 4-lactone, to inhibit beta-glucuronidase, thereby increasing the net glucuronidation of the retinoid. There is also evidence that the retinoid glucuronide is biologically active and inhibits tumor cell growth, Zile et al., Proc.

Natl. Acad. Sci. USA 84:2208–2212 (1987), Gallup et al., Proc. Soc. Exptl. Biol. Med. 186:269–274 (1987). However, though it may be less cytotoxic than the parent retinoid it may not be significantly more cytostatic. In any event, this novel combination of natural metabolites or combinations or glucarate and retinoid are highly effective in the prevention and treatment of cancer in this and other model systems.

It may be advantageous to formulate the compositions of the invention in unit dosage form for ease of administration and uniformity of dosage. A unit dosage formed, as used herein, refers to a physically discrete unit suitable for use as a unitary dosage for the mammalian subjects to be treated; each unit contains a predetermined quantity of active material calculated to produce the desired therapeutic effect, in association with the required pharmaceutically acceptable carrier. Specifications for unit dosage forms are dictated by and directly dependent on (a) the unique characteristics of the active material in the particular therapeutic affect to be achieved, and (b) the limitations inherent in the art of compounding such an active material for the treatment of disease in living subjects having a diseased condition, without excessive cytotoxic effects.

Regression of breast cancer and inhibition of tumor growth may be obtained, for example, by the use of daily dosing for up to 50 to 100 days, or longer. Multiple dosing, or dosing on any desired periodic basis, may also be utilized. The therapeutically active ingredient is thus administered in an amount sufficient to aid regression and inhibition of further growth of the cancer, in the absence of excessive deleterious side-effects of a phyto-toxic nature.

The minimum dosage of the anticarcinogens used alone, consistent with maximum inhibition of carcinogenesis is approximately equivalent to 4 gm % CGT (4 gm/100 gm of chow diet) or 1.0–1.5 mmol/kg of HPR. This consideration is important since the human (in proportion to the surface area of the rodent) would need to consume approximately 40 gm of CGT per day while a dosage of 1.5 mmol/kg of retinoid would result in cummulative toxicity, with excess being deposited in the liver. Thus previous studies have been hindered by concern and actual problems with the toxicity of effective doses of the retinoids. The problems common to the use of these two classes of anticarcinogens when used separately, is circumvented by their combination. Furthermore, since their efficacy was tested using a carcinogenic protocol which utilized a single high dose of carcinogen (the minimum effective dose), it may be possible to reduce their concentrations even lower under chronic dose exposure to carcinogens. Thus, we have found that a combination of 1–2% CGT and 0.75–1.0 mmol/kg of retinoid is as effective as the single higher doses of each.

The anticarcinogenic compounds (active ingredients) of this invention can be administered to inhibit the formation of tumor cells or to decrease the risk of contracting cancer by any means that produces contact of the active ingredient with the agents site of action in the body of a human or animal. They can be administered by any conventional means available for use in conjunction with pharmaceuticals, either as individual therapeutic active ingredients or a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of receipient; nature and extent of symptoms, kind of concurrent treatment, frequency of treatment, and the effects desired. Usually a daily dosage of active ingredient can be about 5–400 mg/kg of body weight. Ordinarily, 10–300, and preferably 100–300 mg/kg body weight per day given in single doses or divided doses 2–4 times a day or in sustained release form is effect to obtain desired results. In a preferred embodiment the dietary supplement comprises approximately 0.01 to 0.02 parts by weight of the glucarolactone-based compounds for inhibiting beta-glucuronidase and approximately 0.0003 to 0.0006 parts by weight of the retinoid-based compound for elevating levels of cellular cAMP and of histone kinases.

Dosage forms (compositions) suitable for internal administration contain from about 1.0 mg to about 500 mg of active ingredient per unit. In these pharmaceutical compositions active ingredient will normally be present in an amount of 0.5–95%, by weight, based on the total weight of the composition.

The active ingredient can be administered in the diet or in solid dosage forms such as capsules, tablets and powders or in liquid dosage form, such as elixers, syrups and suspensions.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of the composition over a period of hours. Compressed tablets can be sugar-coated or film-coated to mask any unpleasant taste and protect the tablet from atmosphere, or enteric-coated for selective disintegration in the gastrointestinal tract.

Liquid dosage forms for oral administration can contain coloring and flavor to increase patient acceptance.

Useful pharmaceutical-dosage forms for administration of the compounds of this invention can be illustrated as follows:

CAPSULES: A large number of unit capsules are prepared by filling standard two-piece hard gelatin capsules each with 100 mg of powdered active ingredient, 175 mg of lactose, 24 mg of talc, and 6 mg magnesium stearate. A mixture of active ingredient in soybean oil is prepared and injected by means of a positive displacement pump into gelatin to form soft gelatin capsules containing 100 mg active ingredient. The capsules are washed and dried.

TABLETS: Large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of cornstarch and 98.8 mg of lactose. Appropriate coatings may be applied to increase pallatability or delayed absorption.

For treatment of non-human animals, the composition is preferably incorporated in animal feed, feed supplements or feed concentrates.

From the preceding, it can be seen that in accordance with the present invention, a novel composition comprising glucarolactone-based compounds and retinoid-based compounds is provided, the members of the compositions of which induce regression and/or inhibit the induction and growth of various malignant tumors in mammals.

It will be apparent that various changes may be made in the method of preparation and use, as well as in the particular substitution of therapeutically active compositions of the present invention. Accordingly, the preceding disclosure should be construed as illustrative only, and the scope of the claims should be incorporated in accordance with the claims appended hereto.

We claim:

1. A dietary supplement for inhibiting the formation or growth of mammary cancer in humans or animals or for decreasing a patient's risk of contracting cancer via steady and prolonged inhibition of beta-glucuronidase and via elevation of the level of cellular cAMP (cyclic AMP) and of histone kinases, consisting essentially of approximately 0.01 to 0.02 parts by weight of calcium glucarate for inhibiting beta-glucuronidase and approximately 0.0003 to 0.0006 parts by weight of 13-cis-retinoic acid for elevating levels of cellular cAMP and of histone kinases.

2. The dietary supplement of claim 1, wherein the daily dosage of the supplement administered is from about 100 to about 300 mg/kg body weight.

3. The dietary supplement of claim 1, wherein the supplement is administered to a patient in a high risk category for mammary cancer.

4. The dietary supplement of claim 1, wherein the supplement is administered promptly after the detection of the cancer.

5. The dietary supplement of claim 1, wherein the human or animal being treated has not contracted cancer.

6. A method for inhibiting the formation or growth of mammary cancer in humans or animals or for decreasing the risk of contracting cancer comprising administering an amount, which is safe and sufficient of the dietary supplement of claim 1, or a pharmaceutically acceptable salt thereof to a patient having cancer or who is at risk for contracting cancer.

7. The method of claim 6, wherein a daily dosage of the supplement administered is from about 100 to about 300 mg/kg body weight.

8. The method according to claim 6, wherein the supplement is administered to a patient in a high risk category for mammary cancer.

9. The method according to claim 6, wherein the supplement is administered promptly after the detection of the cancer.

10. The method according to claim 6, wherein the human or animal being treated has not contracted cancer.

11. A pharmaceutical composition which comprises a therapeutically effective amount of the supplement of claim 1 in admixture with a pharmaceutically acceptable, substantially non-toxic carrier or excipient.

* * * * *